United States Patent [19]
McKinley et al.

[11] Patent Number: 4,976,152
[45] Date of Patent: Dec. 11, 1990

[54] 3 POINT BENDING MEASURING SYSTEM

[75] Inventors: Kerry McKinley, Danbury, Conn.; Benjamin Twombly, Basking Ridge, N.J.

[73] Assignee: The Perkin Elmer Corporation, Norwalk, Conn.

[21] Appl. No.: 435,114

[22] Filed: Nov. 13, 1989

[51] Int. Cl.⁵ ............................................. G01N 3/20
[52] U.S. Cl. ................................................... 73/852
[58] Field of Search .......................... 73/812, 849–853, 73/856, 860

[56] References Cited

U.S. PATENT DOCUMENTS

| | | | |
|---|---|---|---|
| 1,200,086 | 10/1916 | Cruser | 73/852 |
| 2,404,584 | 7/1946 | Liska et al. | 73/852 |
| 2,670,624 | 3/1954 | Faris, Jr. et al. | 73/852 |
| 4,320,651 | 3/1982 | Tordoff | 73/852 |
| 4,589,288 | 5/1986 | Porter et al. | 73/852 |
| 4,763,529 | 8/1988 | Leonard et al. | 73/852 |

FOREIGN PATENT DOCUMENTS 1216704  3/1986  U.S.S.R. ................................. 73/849

OTHER PUBLICATIONS

Wachtman, Jr. et al., "Biaxial Flexure Tests of Ceramic Substrates", Journal of Materials, vol. 7, No. 2, Jun. 1972, pp. 188–194.

Primary Examiner—Robert Raevis
Attorney, Agent, or Firm—Edwin T. Grimes; Thomas P. Murphy

[57] ABSTRACT

A sample holder for use with a bending measuring system. A probe shaft is disposed in an elongated tube. A probe tip is removeably mounted at one end of the probe shaft. The other end of the probe shaft is adapted to be fixed to the bending measuring system. A double knife edge platform supports a sample at each end and the probe tip contacts the sample at its center. Proper alignment between the sample and probe tip is obtained by having means which permit radial adjustment of the platform and rotation of the probe shaft about its central axis.

5 Claims, 1 Drawing Sheet

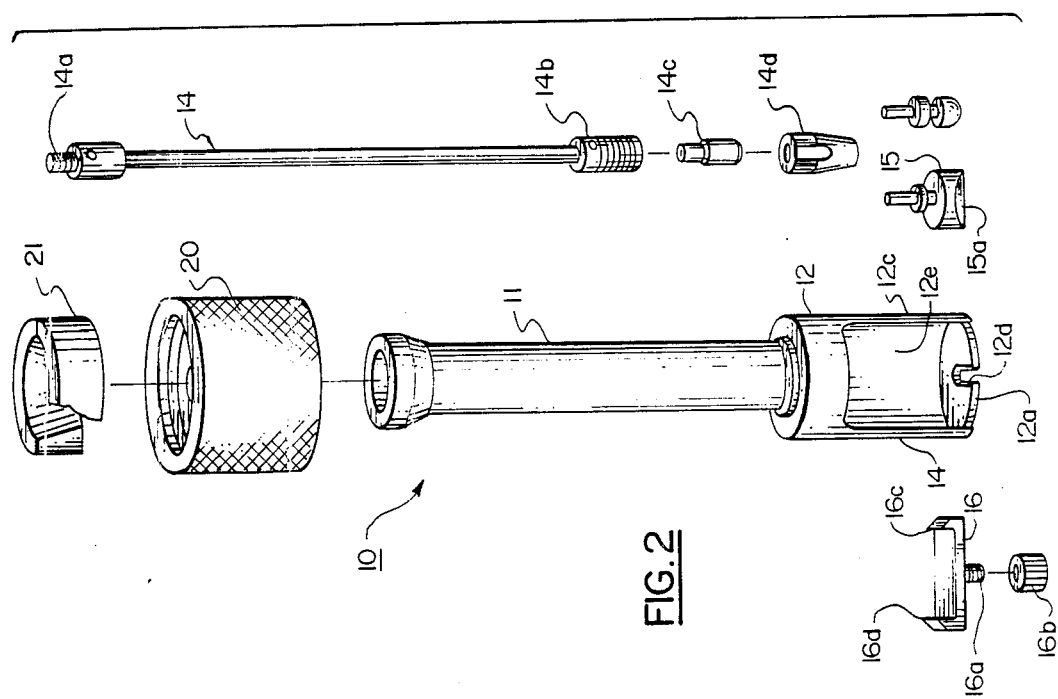
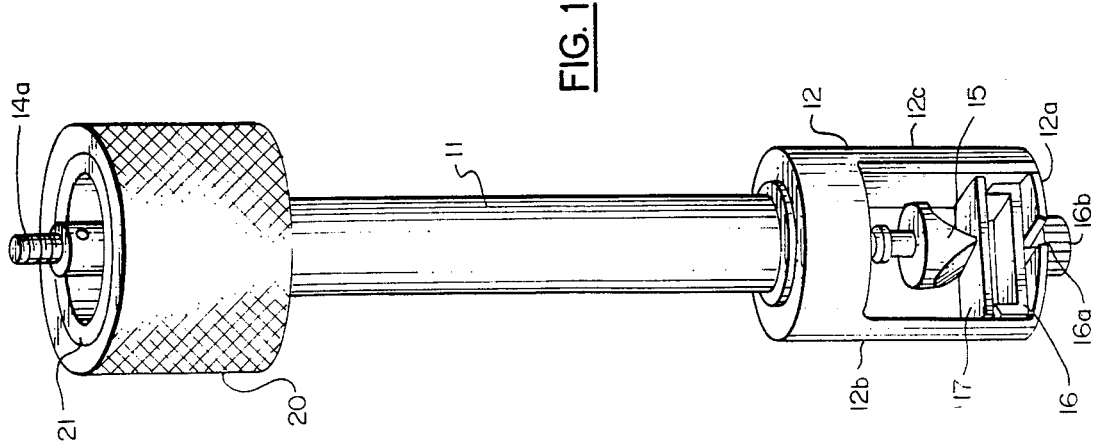

3 POINT BENDING MEASURING SYSTEM

BACKGROUND OF THE INVENTION

One type of material testing comprises bending an elongated, thin sample specimen under controlled conditions. Typically, the sample is mounted so that a probe contacting the center of the sample can apply a predetermined reciprocal bending force at a predetermined frequency. By measuring the frequency and amplitude response of the sample and comparing them with the driving force and frequency of the bending motor many properties of the sample material can be determined. These properties include the storage and loss moduli, the complex viscosity and tan delta. However, the manner of sample holding is critical. Previous sample holders often make precise centering of the probe tip difficult. Interchangeability and access to the probe tip also pose serious problems.

BRIEF DESCRIPTION OF THE INVENTION

The present invention relates to a sample holder wherein the probe tip is easily and precisely centered relative to the sample and the probe tip itself is accessible and easily replaced by probe tips more suitable to the particular sample under test.

Briefly, the present invention comprises a probe holder having a probe tip at one end. A double knife edge platform supports a relatively thin sample at each of its ends while the probe tip contacts the sample at its center to provide the bending force as well as to fix the sample in place against the two knife edges of the double knife edge platform. Precise alignment of the probe tip on the sample is obtained by means which permit radial adjustment of the platform and rotation of the probe holder about its central axis.

BRIEF DESCRIPTION OF THE DRAWINGS

FIG. 1 is an isometric pictorial drawing of the sample holder of the present invention; and FIG. 2 is an assembly drawing of the sample holder of the present invention.

DESCRIPTION

Referring to FIGS. 1 and 2 there is shown the sample holder assembly 10 of the present invention. It comprises an elongated tube 11. At one end of the tube 11 there is a sample container 12 which may be integral or otherwise fixedly attached to tube 11. The sample container 12 has a larger diameter than tube 11 and has a flat end 12a supported by arms 12b and 12c. Flat end 12a has a radial slot 12d to assist in positioning a sample in a manner to be explained fully hereinbelow. The arms 12b and 12c are of equal size opposite each other and small enough to define opposite openings 12e which make for easy accessibility to the sample container 12.

Fixed to the other end of tube 11 is a collar 20. The collar 20 may be fixed to tub 11 in any convenient manner, e.g., threaded or force fitted or otherwise fixed. A ferrule 21 may be inserted into collar 20 which may be internally threaded for attachment to the actual measuring system assembly (not shown). The actual measuring system assembly, while not part of the present invention, would include a reciprocating motor attached to the probe shaft for bending the sample at a given frequency and amplitude. It would also include means for measuring the frequency and amplitude of the sample bending and comparing this data to a known or calculated standard.

A probe shaft 14 is disposed in tube 11. One end of probe shaft 14 is adapted for connection to the measuring system, e.g., by threaded end 14a.

The other end 14b of the probe shaft 14 extends into sample container 12. A probe tip, e.g., a probe tip similar to probe tip 15 is removably fixed to this end of probe shaft 14 via, e.g., a collet 14c and chuck 14d.

A bending platform similar to bending platform 16 shown in FIGS. 1 and 2 together with probe tip 15 hold a sample, e.g., sample 17 fixed at three points - edges 16c and 16d of bending platform 16 and edge 15a of probe tip 15 as seen in FIG. 2.

Bending platform 16 is fixed to flat end 12 by means of slot 12d and knurled nut 16b and threaded extension 16a thereof which fits into slot 12d. This arrangement provides a three point sample holder for use in a bending measuring system. The slot 12d permits radial adjustment of the bending platform 16 while rotatability of probe tip 15 as well as sample tube assembly 11 about its longitudinal axis provide rotational adjustment of the probe tip 15 relative to the sample 17. This construction of the sample holder allows the probe tip 15 to be centered precisely on the sample 17.

The design of the sample holder assembly 10 allows the use of different probe tips 15, e.g., for different sample stiffnesses by changing contact area from an edge which differs in length down to a point. The present invention also reduces thermal lag and provides a uniform temperature gradient in the sample area. A relatively low thermal lag due to its low thermal mass uniform gradient is due to the symmetry of the measuring system.

Other modifications of the present invention are possible in light of the above description which should not be deemed as limiting the invention beyond the limitations expressly set forth in the claims which follow:

What is claimed is:

1. A sample holder for use with a bending-measuring system, comprising:
   a sample container comprising two arms;
   a plate supported by said two arms forming the bottom of said sample container;
   said two arms forming access windows into said sample container;
   a probe shaft rotatable about its axis having one end disposed in said sample container and the other end fixed to the bending-measuring system;
   a probe tip removably fixed to said one end of said probe shaft disposed in said sample container;
   a platform fixed to said sample container supporting said sample at two regions;
   said probe tip holding said sample against and central to said two points of said platform;
   a slot in said plate;
   a threaded screw fixed to said platform disposed in said slot such that said screw and said platform are radially moveable relative to said plate and said probe tip; and
   nut means adapted to be tightened on said screw to hold said platform fixed relative to said plate and probe tip at a desired position.

2. A sample holder according to claim 1 wherein said two regions are knife edges for contacting said sample.

3. A sample holder according to claim 2 wherein said probe tip terminates in a knife edge for contacting said sample.

4. A sample holder according to claim 3 further comprising:
an elongated tube having said sample container fixed to one end and said probe shaft rotatably disposed therein.

5. A sample holder according to claim 4, wherein:
said probe tip and platform can accommodate samples of various thicknesses and lengths and are both adjustable relative to a predetermined position.

* * * * *